US008918207B2

(12) United States Patent
Prisco

(10) Patent No.: US 8,918,207 B2
(45) Date of Patent: Dec. 23, 2014

(54) OPERATOR INPUT DEVICE FOR A ROBOTIC SURGICAL SYSTEM

(75) Inventor: Giuseppe M. Prisco, Mountain View, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 1226 days.

(21) Appl. No.: 12/400,728

(22) Filed: Mar. 9, 2009

(65) Prior Publication Data

US 2010/0228265 A1    Sep. 9, 2010

(51) Int. Cl.
*G06F 19/00* (2011.01)
*B25J 9/16* (2006.01)
*A61B 19/00* (2006.01)

(52) U.S. Cl.
CPC ........ *B25J 9/1689* (2013.01); *A61B 2019/2296* (2013.01); *A61B 2019/2211* (2013.01); *G05B 2219/39389* (2013.01); *G05B 2219/45117* (2013.01); *G05B 2219/39387* (2013.01); *A61B 19/2203* (2013.01)
USPC ................. 700/245; 606/1; 606/90; 606/130; 606/185; 318/568.11; 5/623; 59/78.1; 74/490.01; 382/224; 382/298; 180/19.1; 434/262; 227/175.1; 600/102; 600/427

(58) Field of Classification Search
USPC ........................ 700/245; 606/1, 90, 130, 185; 318/568.11; 5/623; 59/78.1; 74/490.01; 382/224, 298; 180/19.1; 434/262; 227/175.1; 600/102, 427
See application file for complete search history.

(56) References Cited

U.S. PATENT DOCUMENTS

| 3,976,061 A | * | 8/1976 | Volkov et al. ................... 606/90 |
| 6,246,200 B1 | | 6/2001 | Blumenkranz et al. |
| 6,364,888 B1 | | 4/2002 | Niemeyer et al. |
| 6,424,885 B1 | | 7/2002 | Niemeyer et al. |
| 6,459,926 B1 | | 10/2002 | Nowlin et al. |
| 6,684,129 B2 | | 1/2004 | Salisbury, Jr. et al. |
| 6,714,839 B2 | | 3/2004 | Salisbury, Jr. et al. |
| 6,726,699 B1 | * | 4/2004 | Wright et al. ................. 606/185 |
| 6,799,065 B1 | | 9/2004 | Niemeyer |
| 7,087,049 B2 | | 8/2006 | Nowlin et al. |
| 2001/0013764 A1 | * | 8/2001 | Blumenkranz et al. .. 318/568.11 |

(Continued)

OTHER PUBLICATIONS

J. Yan and S.E Salcudean; Design and Control of a Motion Scaling System for Microsurgery Experiments; Department of Electrical Engineering, University of British Columbia; Vancouver, BC, V6t 1Zf, Canada.

(Continued)

*Primary Examiner* — James Trammell
*Assistant Examiner* — Sanjeev Malhotra

(57) ABSTRACT

A robotic surgical system includes a master controller with an input handle and robotic manipulator assemblies including a surgical end effector and an endoscopic camera. The input handle is translatable to provide a position and rotatable to provide an orientation. A control system couples the master controller to the first and second manipulator assemblies. The control system moves the surgical end effector in response to the position and orientation of the input handle. The control system moves the input handle to orient the input handle to correspond to an orientation of the surgical end effector from a viewpoint of the endoscopic camera during the repositioning of at least one of the input handle position, the end effector, or the endoscopic camera. The control system may move the surgical end effector only in a first mode and orients the input handle only in a second mode.

32 Claims, 4 Drawing Sheets

(56) References Cited

U.S. PATENT DOCUMENTS

| | | | |
|---|---|---|---|
| 2002/0082612 A1* | 6/2002 | Moll et al. | 606/130 |
| 2002/0128552 A1* | 9/2002 | Nowlin et al. | 600/427 |
| 2002/0147527 A1* | 10/2002 | McCall et al. | 700/245 |
| 2003/0172460 A1* | 9/2003 | Schuerch | 5/623 |
| 2006/0069383 A1* | 3/2006 | Bogaerts et al. | 606/1 |
| 2006/0201130 A1* | 9/2006 | Danitz | 59/78.1 |
| 2007/0089557 A1* | 4/2007 | Solomon et al. | 74/490.01 |
| 2007/0147707 A1* | 6/2007 | Coste-Maniere et al. | 382/298 |
| 2007/0156121 A1* | 7/2007 | Millman et al. | 606/1 |
| 2007/0163816 A1* | 7/2007 | Schena et al. | 180/19.1 |
| 2007/0172803 A1* | 7/2007 | Hannaford et al. | 434/262 |
| 2007/0185376 A1* | 8/2007 | Wilson et al. | 600/102 |
| 2008/0021440 A1* | 1/2008 | Solomon | 606/1 |
| 2008/0308601 A1* | 12/2008 | Timm et al. | 227/175.1 |
| 2009/0247819 A1* | 10/2009 | Wilson et al. | 600/102 |
| 2009/0287223 A1* | 11/2009 | Pua et al. | 606/130 |
| 2010/0195919 A1* | 8/2010 | Coste-Maniere et al. | 382/224 |

OTHER PUBLICATIONS

M.W. Thring; Robots and Telechris: Manipulators with Memory; Remote Manipulators; Machine Limbs for the Handicapped; Ellis Horwood Limited; Chichester, West Sussex P019 1EB England; pp. 9-11, 108-131, 194-195, 235-279; 1983.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

* cited by examiner

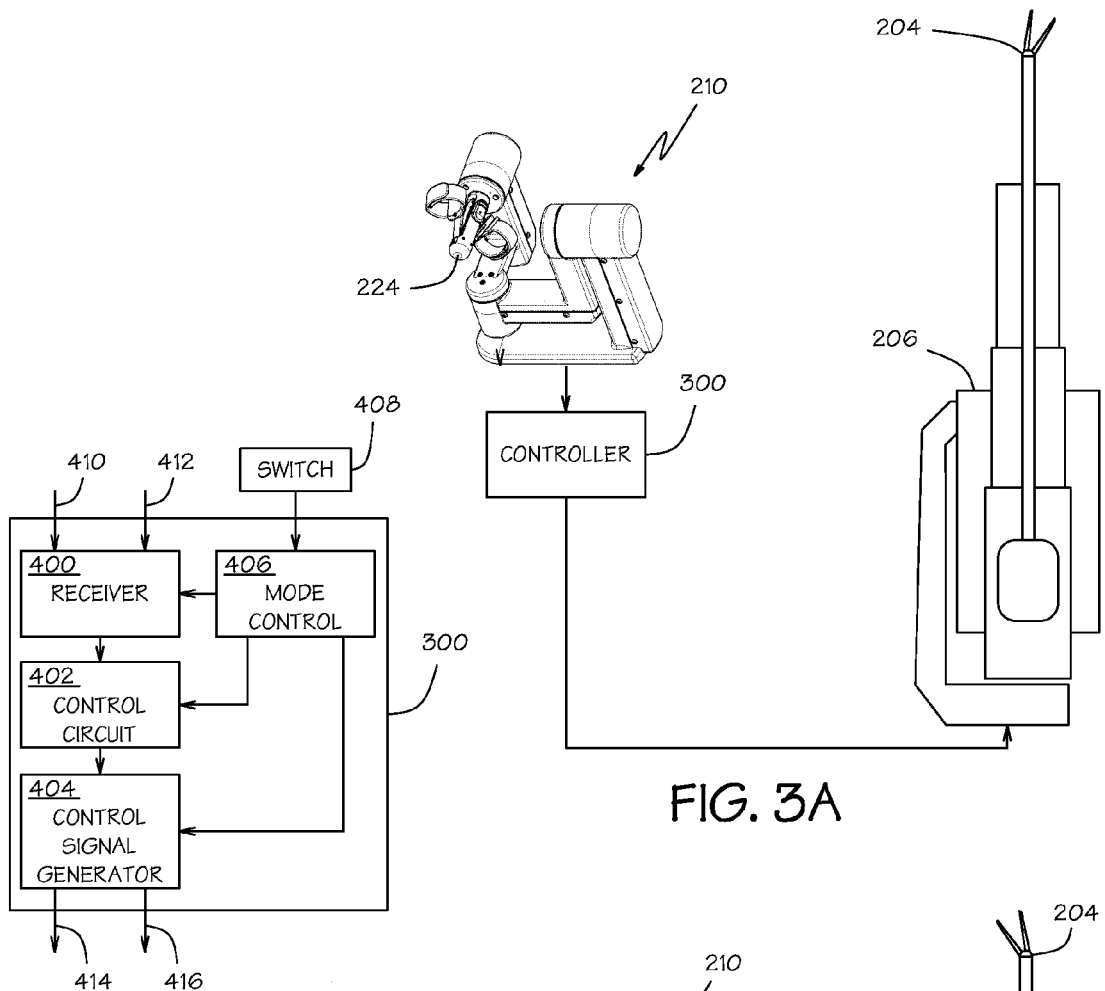
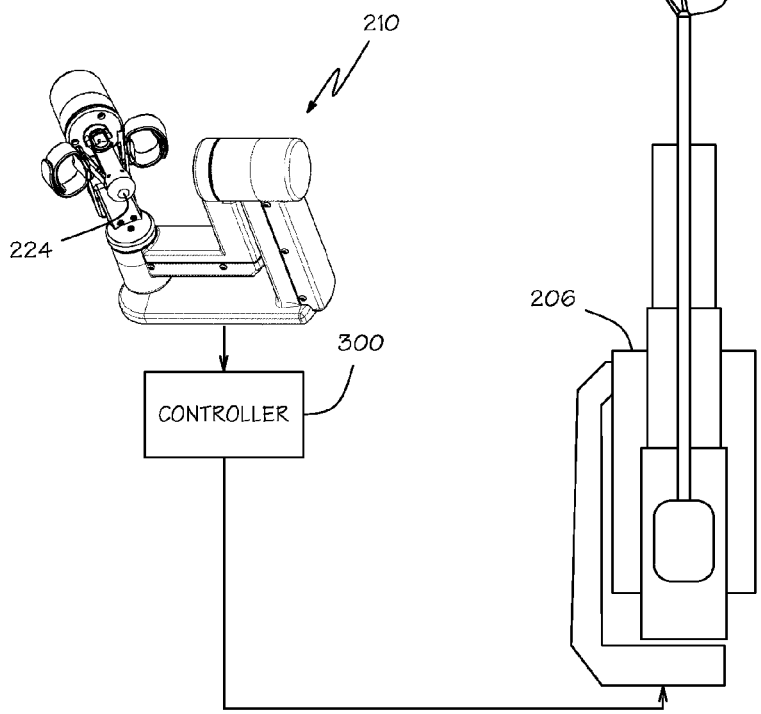

OPERATOR INPUT DEVICE FOR A ROBOTIC SURGICAL SYSTEM

BACKGROUND

1. Field

This invention relates to data input devices, and more particularly, to a master controller which may be used for directing movements of a robot and which is particularly useful for robotically enhanced surgery.

2. Background

In robotically assisted surgery, the surgeon typically operates a master controller to remotely control the motion of surgical instruments at the surgical site. The master controller may be separated from the patient by a significant distance (e.g., across the operating room, in a different room, or in a completely different building than the patient). Alternatively, a master controller may be positioned quite near the patient in the operating room. Regardless, the master controller will typically include one or more hand input devices.

These hand input devices are coupled by a servo mechanism to the surgical instrument. More specifically, servo motors move a manipulator or "slave" supporting the surgical instrument based on the surgeon's manipulation of the hand input devices. During an operation, the surgeon may employ, via the robotic surgery system, a variety of surgical instruments such as tissue graspers, needle drivers, electrosurgical cautery probes, etc. Each of these structures performs functions for the surgeon, for example, holding or driving a needle, grasping a blood vessel, or dissecting, cauterizing, or coagulating tissue.

To deliver the full potential of this new form of surgery, the robotic system will preferably allow movement of the surgical end effector in both position and orientation. Directing such robotic input is much easier when the surgeon is able to move the hand input device with motions that correspond to the desired motions of the end effector. In particular, it is desirable to maintain a substantial correspondence between the orientation of the hand input device and the end effector.

One obstacle to maintaining a substantial correspondence between the orientation of the hand input device and the surgical end effector is the need to reposition elements of the robotic surgical system during surgery. For example, it may be necessary to reposition an endoscopic camera to gain a better view of the surgical field. Repositioning the camera will change the perceived orientation of the surgical end effector and thus end the substantial correspondence between the orientation of the hand input device and the end effector as seen by the surgeon in a visual display at the master controller.

Existing robotic surgical systems may provide a first mode in which the hand input device controls the surgical end effector and a second mode that allows elements to be repositioned. The orientation of the hand input device may be adjusted when changing from the second mode to the first mode to restore the substantial correspondence between the orientation of the hand input device and the end effector. While this is effective, adjusting the orientation of the hand input device may take a significant amount of time because it is undesirable to move the hand input device abruptly. In many surgical procedures it is desirable to reposition elements of the robotic surgical system fairly frequently. Thus adjusting the orientation of the hand input device may consume a substantial amount of time and disrupt the progress of the surgical procedure.

In light of the above, it would be desirable to provide an improved apparatus and method for orienting an operator input device for a robotic surgical system when elements of the system are repositioned.

SUMMARY

A robotic surgical system includes a master controller with an input handle and robotic manipulator assemblies including a surgical end effector and an endoscopic camera. The input handle is translatable to provide a position and rotatable to provide an orientation. A control system couples the master controller to first and second manipulator assemblies. The control system has first and second modes. In the first mode, the control system moves the surgical end effector in response to the position and orientation of the input handle. In the second mode, the control system allows repositioning of at least one of the input handle position, the end effector, or the endoscopic camera and moves the input handle to orient the input handle to correspond to an orientation of the surgical end effector from a viewpoint of the endoscopic camera during the repositioning.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 3A is a schematic view of the operator input device connected to a manipulator that controls a surgical instrument.

FIG. 3B is a schematic view of the operator input device and the surgical instrument in a second position.

FIG. 4 is a block diagram of a controller that controls an operator input device and a surgical instrument.

DETAILED DESCRIPTION

In the following description, numerous specific details are set forth. However, it is understood that embodiments of the invention may be practiced without these specific details. In other instances, well-known devices, structures and techniques have not been shown in detail in order not to obscure the understanding of this description.

As used herein, first and second objects (and/or their images) appear "substantially connected" if a direction of an incremental positional movement of the first object matches the direction of an incremental positional movement of the second object (often as seen in an image), regardless of scaling between the movements. Matching directions need not be exactly equal, as the objects (or the object and the image) may be perceived as being connected if the angular deviation between the movements remains small. Similarly, objects and/or images may be perceived as being "substantially and orientationally connected" if they are substantially connected and if the direction of an incremental orientational movement of the first object is matched by the direction of an incremental orientational movement of the second object (often as seen in an image displayed near the first object), regardless of scaling between the movements.

Additional levels of connectedness may, but need not, be provided. "Magnitude connection" indicates substantial connection and that the magnitude of orientational and/or positional movements of the first object and second object (typically as seen in an image) are directly related. The magnitudes need not be equal, so that it is possible to accommodate scaling and/or warping within a magnitude connected robotic system. Orientational magnitude connection will imply substantial and orientational connection as well as related orientational movement magnitudes, while substantial and magnitude connection means substantial connection with positional magnitudes being related.

As used herein, a first object appears absolutely positionally connected with an image of a second object if the objects are substantially connected and the position of the first object and the position of the image of the second object appear at least to substantially match, i.e., to be at the same location, during movement. A first object appears absolutely orientationally connected with an image of the second object if they are substantially connected and the orientation of the first object and the second object at least substantially match during movement.

Figure 1:
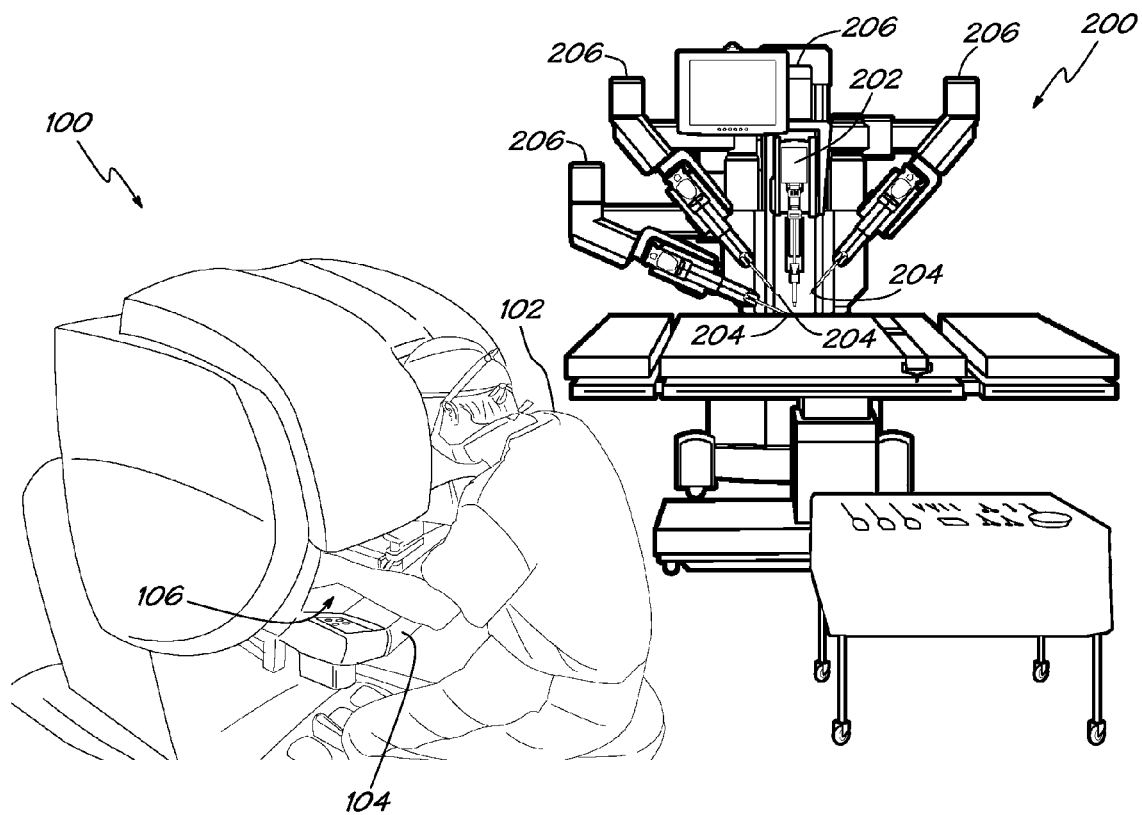
FIG. 1 is a perspective view of a master control workstation and a manipulator system for robotically moving a plurality of minimally invasive surgical instruments.

Referring to FIG. 1, a robotic surgical system includes a master controller 100 and a patient side cart 200, along with any of several other additional components to enhance the capabilities of the robotic devices to perform surgical procedures. A surgeon 102 performs a minimally invasive surgical procedure at an internal surgical site within a patient (not shown) using minimally invasive surgical instruments 204. The surgeon 102 works at the master controller 100. The surgeon 102 views a visual display, such as a stereoscopic video display, provided by the master controller 100 and manipulates left and right input devices. The robotic surgical system moves the surgical instruments 204 mounted on robotic manipulators 206 of the patient side cart 200 in response to the surgeon's 102 movement of the input devices.

Each robotic manipulator 206 can be operatively connected to one or more of the input devices so that the movement of an instrument mounted on the robotic manipulator is controlled by manipulation of the connected input device. The instruments carried on the robotic manipulators 206 have end effectors, generally indicated at 204, which are mounted on wrist members. The wrists are in turn pivotally mounted on distal ends of elongate shafts of the instruments. It will be appreciated that the instruments have elongate shafts to permit them to be inserted into an internal surgical site of a patient's body. Movement of the end effector relative to the end of the shaft of the instrument is also controlled by the connected input device.

A control system couples the master controller 100 to the robotic manipulators 206. As described in more detail in U.S. Pat. No. 6,424,885 entitled "Camera Referenced Control In A Minimally Invasive Surgical Apparatus," the full disclosure of which incorporated herein by reference, the control system will preferably coordinate movement of the input devices with the movement of their associated surgical instruments so that the images of the surgical instruments 204, as displayed to the surgeon 102, appear at least substantially connected to the input devices in the hands of the surgeon. Further levels of connection will also often be provided to enhance the surgeon's dexterity and ease of use of the surgical instruments 204.

The surgeon 102 may actively control two surgical tools 204 while a third remains at a fixed position, for example an endoscopic camera 202 may normally be held in a fixed position by the robotic manipulator 206 with the surgeon selectively moving the endoscopic camera intermittently as necessary to change the point of view of the surgical field. Additional surgical tools 204 may be provided that are normally held at a fixed position, for example a retractor, spreader, or tissue stabilizer. The surgeon 102 may selectively move the additional surgical tools intermittently as necessary. The control system of the master controller 100 may allow the input devices the be selectively connected to the various robotic manipulators 206 so that any of the associated surgical tools may be moved under the control of the surgeon 102 as required.

Figure 2:
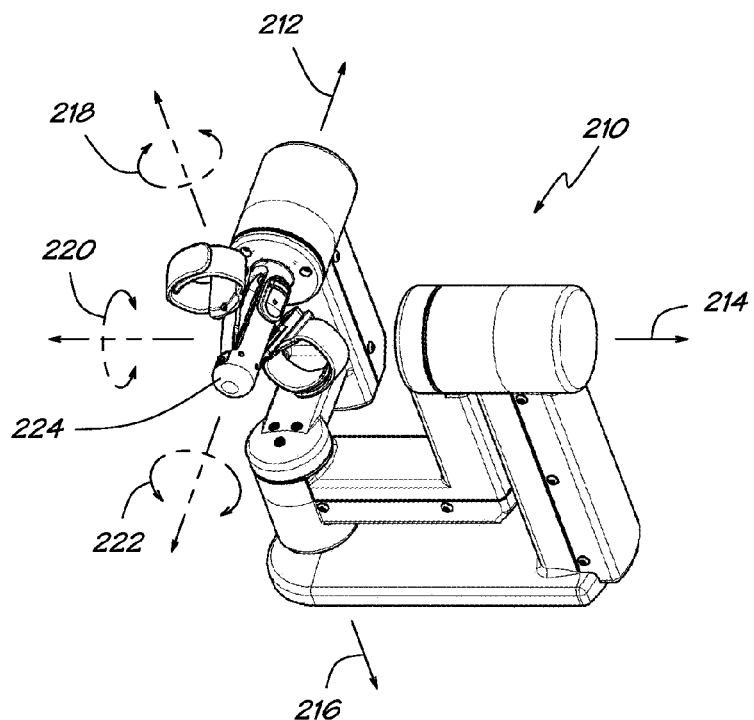
FIG. 2 is a perspective view of an operator input device used in the master control workstation shown in FIG. 1.

FIG. 2 shows an input device 210 that may be used in the master controller 100. The master controller may include two such input devices. One of the input device may be in an opposite configuration to provide a right and left hand input device. The input device 210 includes an input handle 224 that may be grasped by the surgeon 102 to control a robotic manipulator 206. The input handle 224 is supported by a plurality of members or links connected together by joints, typically by rotational joints. The surgeon may grip the input handle 224 by positioning his or her thumb and index finger over a grip actuation handle, shown here in the form of a grip handle or pincher formation. The surgeon's thumb and index finger are typically held on the pincher formation by straps. To move the orientation of the end effector, the surgeon simply moves the pincher formation to the desired surgical end effector orientation relative to the image viewed at the master controller 100, and the surgical end effector orientation is caused to follow the orientation of the pincher formation. Appropriately positioned positional sensors, e.g., encoders, or potentiometers, or the like, are coupled to each joint of gimbals, so as to enable joint positions of the input device 100 to be determined as also described in greater detail herein below.

The input handle 224 is movable in a plurality of degrees of freedom, typically with six degrees of freedom, three translational degrees of freedom and three rotational degrees of freedom. The input handle may be constructed as described in more detail in U.S. Pat. No. 6,714,839 entitled "Master Having Redundant Degrees of Freedom," the full disclosure of which incorporated herein by reference. The input handle 224 is translatable to provide a position of the input handle as suggested by the three straight arrows 212, 214, 216. The input handle 224 is further rotatable in a plurality of degrees of freedom to provide an orientation of the input handle as suggested by the three curved arrows 218, 220, 222.

Some or all of the joints supporting the input handle 224 may be active joints that can be positioned by the control system. The control system can selectively relinquish control of any of the active joints and allow the surgeon 102 to position that joint using the input handle 224. In particular, the control system can selectively control the joints that establish the orientation of the input handle 224.

FIG. 3A is a schematic view of the operator input device 210 connected to a robotic manipulator 206 that controls a surgical instrument 204. The input device 210 is coupled to the robotic manipulator 206 by a controller 300. FIG. 3B is a schematic view of the operator input device and the surgical instrument in a second position. While the end effector 204 is shown as having a pair of operative parts, such as a scissors, pliers, needle driver, or clamp, it should be understood that the surgical instrument may have a single operative part, such as a scalpel, cautery electrode, or aspirator.

FIG. 4 is a block diagram of the controller 300. A receiver 400 portion of the controller 300 is coupled to the input handle 224 of the input device 210. The receiver 400 receives an input handle position signal as the input handle 210 is translated in a plurality of degrees of freedom as suggested by the three straight arrows 212, 214, 216 of FIG. 2. The receiver 400 further receives an input handle orientation signal as the input handle is rotated in a plurality of degrees of freedom as suggested by the three curved arrows 218, 220, 222 of FIG. 2.

A control circuit 402 of the controller 300 is coupled to the receiver 400 portion and to a control signal generator 404. The control signal generator 404 is coupled to the robotic manipulator 206 that moves the surgical end effector 204. The control signal generator 404 may receive signals from the robotic manipulator 206 and/or the surgical end effector 204 to obtain feedback on the position of the surgical end effector.

The control circuit 402 may use the difference between the input handle position and orientation and the position of the surgical end effector to cause the control signal generator 404 to provide signals to the robotic manipulator 206 to cause the surgical end effector 204 to move according to the movements of the input handle 224. The control circuit 402 may be a proportional-integral-derivative controller (PID controller) that provides a control loop feedback mechanism. FIGS. 3A and 3B show the input handle 224 in two different orientations with the orientation of the surgical end effector 204 tracking the orientation of the input handle.

It will be appreciated that the movements of the robotic manipulator 206 and the surgical end effector 204 are likely to be constrained by the need to avoid translation of the instrument where it passes through the patient's skin. Therefore, the controller 300 may provide a translation from the system of motion for the input handle 224 to a different system of motion for the robotic manipulator 206 and the surgical end effector 204. To provide the desired substantial connection between the surgical end effector images and the master controller input devices, the controller 300 will generally map the instrument Cartesian workspace viewed by the endoscope 202 onto the master controller work space in which the surgeon works. The position of the arms holding the surgical tools relative to the arm holding the endoscope in use may be used to derive the desired Cartesian coordinate transformations so as to provide the desired level of substantial connectedness as described in U.S. Pat. No. 6,424,885, which has been incorporated by reference.

The control circuit 402 may further include a mode control 406 coupled to a switch 408. The switch may be a finger operated switch on the input handle 224, a foot operated switch, a switch on the PSM or PSM set up joint or other mechanism equivalent to a switch that allows the surgeon to control the operative mode of the controller 300. The mode control 406 may change which of several input devices 410, 412 is connected to the receiver 400, which of several output devices 414, 416 is connected to the control signal generator 404, and which of several control functions is provided by the control circuit 402. While two selectable inputs 410, 412 and two selectable outputs 414, 416 are shown in the figure, a greater number of inputs and/or outputs may be provided for selection by the mode control 406.

The controller 300 provides for positioning the surgical end effector 204 in response to the input handle position signal and the input handle orientation signal. This allows the surgeon to control the remote surgical instruments in an intuitive fashion that is similar to the way the instruments would be controlled directly in an open surgery. Positioning of the surgical end effector 204 by the controller 300 may be limited so that it only occurs only if the mode control 406 is in a first mode.

The controller 300 further provides for orienting the input handle 224 to correspond to the orientation of the corresponding surgical instrument 204 continuously when the instrument is repositioned by means other than the operation of the controller, such as manual repositioning at the instrument. Orienting the input handle 224 may be limited so that it only occurs only if the mode control 406 is in a second mode. The second mode may further allow at least one of the input handle position, the surgical end effector, or the endoscopic camera to be repositioned while the first mode prevents motion except as effected by the controller 300.

The input device 210 includes an input handle servo mechanism that can orient the input handle 224. The control signal generator 404 may be coupled to the input handle servo mechanism to drive one or more active joints that control the orientation of the input handle 224 such that the orientation of the input handle can be controlled by the controller 300. By continuously changing the orientation of the input handle 224 to correspond to the orientation of the surgical end effector 204 from a viewpoint of an endoscopic camera 202 during the repositioning, it may be possible for the surgeon to change between operative modes of the controller more quickly and with less disturbance to the surgeon's hands.

Figure 5A:
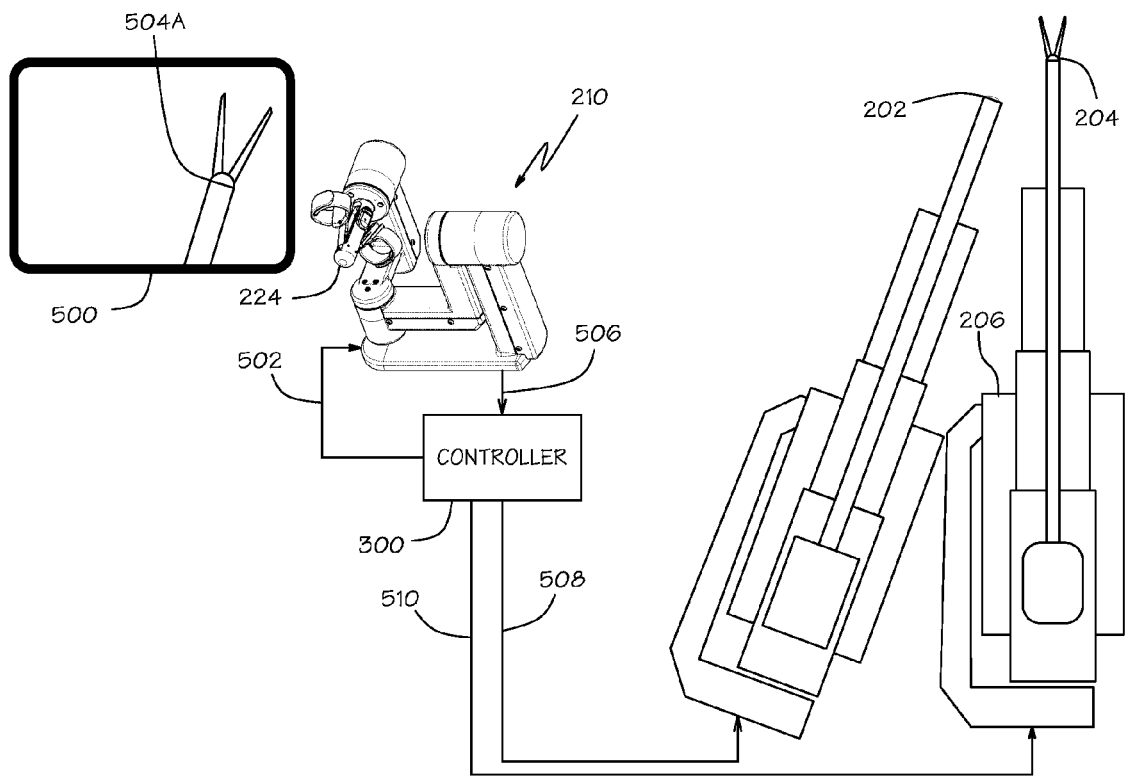
FIG. 5A is a schematic view of the operator input device connected to a manipulator that controls an endoscopic camera to provide an image of the surgical instrument.
Figure 5B:
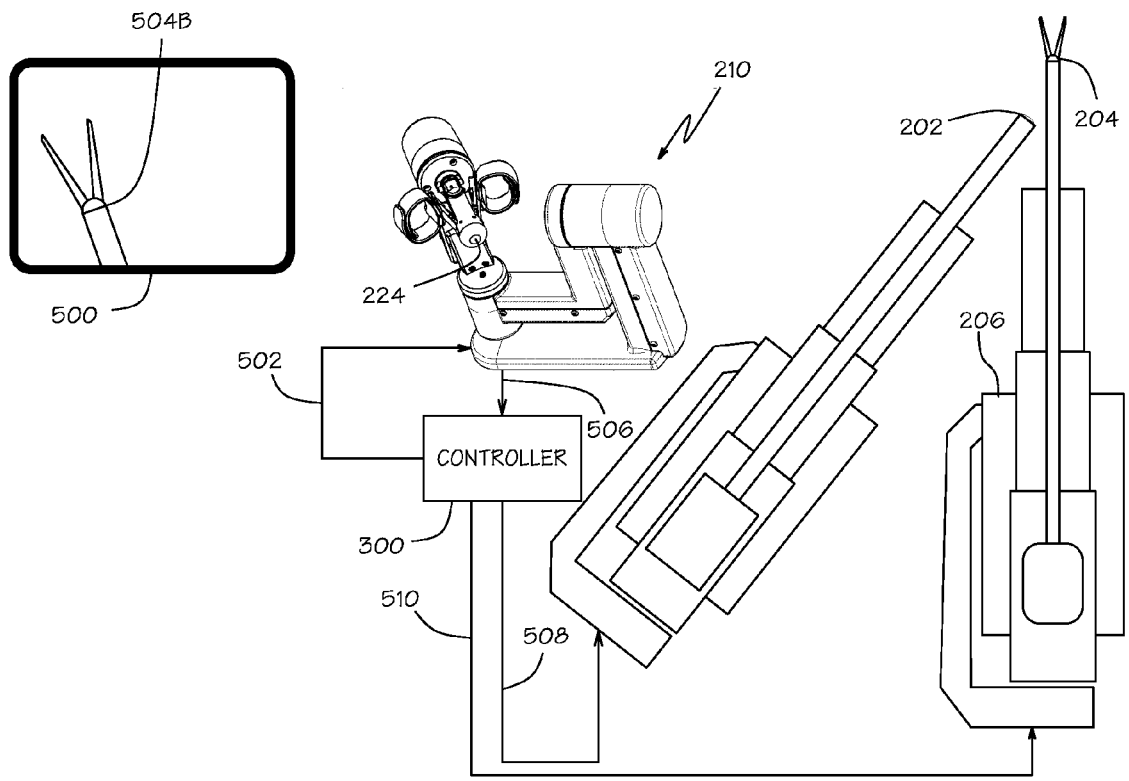
FIG. 5B is a schematic view of the operator input device and the endoscopic camera in a second position.

FIGS. 5A and 5B are a schematic views of the operator input device 210 and the robotic manipulator 206 in an exemplary second operative mode as selected by the mode control 406 responsive to the switch 408. In the mode shown in the figures, the input device 210 controls the position of the endoscopic camera 202 that provides an image 504A of the surgical instrument 204 on a visual display 500. The endoscopic camera 202 has a viewing end at a remote end of an elongate shaft. The elongate shaft of the endoscopic camera 202 permits it to be inserted into an internal surgical site of a patient's body. The endoscopic camera 202 is operatively connected to the master controller 100 to display an image 504A captured at the camera's viewing end. The image 504A of the surgical instrument 204 may be provided by a video display 500 in the master controller 100 for viewing by the surgeon as the remote surgical instruments are manipulated.

The surgical end effector 204 carried on a robotic arm 206 is caused to perform movements and actions in response to movement and action inputs of its associated input handle 224. It will be appreciated that during a surgical procedure images 504A, 504B of the end effector 204 are captured by the endoscope 202 together with the surgical site and are displayed on the viewer 500 so that the surgeon sees the movements and actions of the end effector as they are controlled by movements of the input handle 224. The relationship between the end effector 204 at the surgical site relative to the endoscope tip 202 as viewed through the viewer 500 and the position of the input handle 224 in the hand of the surgeon relative to the surgeon's eyes at the viewer provides an appearance of at least a substantial connection between the input handle and the surgical instrument for the surgeon.

To provide the desired substantial connection between the surgical end effector images 504A, 504B and the input handle 224, the controller 300 will generally map the surgical instrument Cartesian workspace as viewed by the endoscope 202 onto the input device 210 work space in which the surgeon's hands move by means of a rigid transformation of the Cartesian space. The position of the robotic arm 206 holding the surgical tool 204 relative to the robotic arm holding the endoscope 202 may be used to derive the desired coordinate transformations so as to provide the desired level of substantial connectedness.

The receiver 400 portion of the controller 300 may be coupled to the input handle 224 of the input device 210 to receive only the input handle position signal 506 as the input handle 210 is translated in a plurality of degrees of freedom as suggested by the three straight arrows 212, 214, 216 of FIG. 2. The control signal generator 404 may be coupled to the robotic manipulator to provide signals 508 that moves the endoscopic camera 202. The control signal generator may provide signals 510 to the first robotic manipulator 206 to inhibit movement of the surgical end effector 204. Translation of the input handle 210 may cause the endoscopic camera 202 to be aimed at different parts of the surgical field. The endoscopic camera 202 may be less articulated than the surgical instrument 204 and may not require the additional input handle orientation signal to fully control the camera position.

As suggested by FIGS. 5A and 5B the orientation of the surgical instrument 204 may appear to change in the displayed images 504A, 504B as the endoscopic camera 202 is moved. The control signal generator 404 may provide signals 502 to the input device 210 to drive one or more active joints that control the orientation of the input handle 224 such that the orientation of the input handle substantially corresponds to the orientation of the surgical instrument 204 from the current point of view of the moving endoscopic camera 202.

In other embodiments, the control signal generator 404 may allow repositioning of the endoscopic camera 202 by means other than the input handle 224, such as a foot operated device, sensing movement of the surgeon's head or eyes, or manually moving the camera without the use of the robotic manipulator. In all cases, the controller 300 receives signals that provide position information for the endoscopic camera 202 such that the controller is able to continuously determine the orientation of the surgical instrument 204 from the point of view of the camera.

In other embodiments, when the second mode is selected the control signal generator allows repositioning of the surgical end effector independently from the input handle. For example, it may be necessary to reposition the robotic manipulator 206 that supports and moves the surgical instrument 204. The robotic manipulator 206 may be supported by set up joints that can be repositioned as necessary to put the manipulator in a desirable position for controlling the surgical instrument 204. The controller 300 may orient the input handle 224 so that it substantially corresponds to the orientation of the surgical instrument 204 as it is repositioned.

When the second mode is selected, the control signal generator 404 may provide signals to the input handle servo mechanism to prevent changes in the position of the input handle and to allow repositioning of at least one of the surgical end effector or the endoscopic camera. in other embodiments, when the second mode is selected, the control signal generator 404 may provide signals to the first robotic manipulator 206 to inhibit movement of the surgical end effector 204 and to allow translational repositioning of the input handle 224.

Figure 6A:
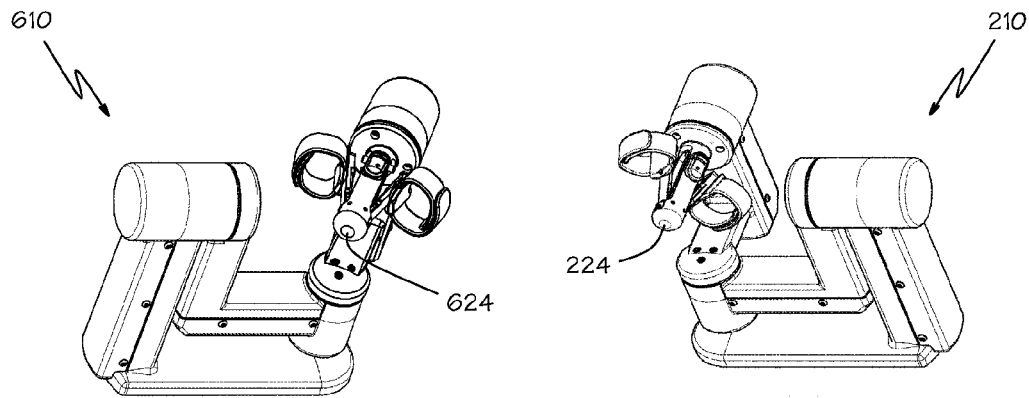
FIG. 6A is a perspective view of two input devices that may be used in the master workstation shown in FIG. 1 to provide a right and left hand input device.
Figure 6B:
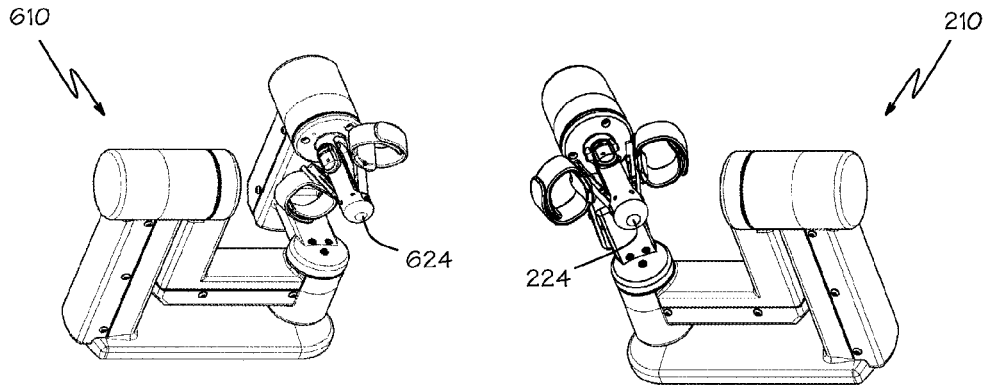
FIG. 6B is a perspective view of the two input devices in a second position.

FIGS. 6A and 6B show two input devices 210, 610 that may be used in the master controller 100 of FIG. 1 to provide a right and left hand input device. The controller 300 may provide a transfer control that allows control of a surgical instrument 204 to be passed from a first input handle 224 of the first input device 210 to a second input handle 624 of the second input device 610. The control signal generator 404 may be coupled to a second input handle servo mechanism that orients the second input handle 624 as suggested by FIGS. 6A and 6B which show the two input devices 210, 610 as the second input handle 624 is oriented to follow the orientation of the first input handle 224.

If the first mode is selected and the transfer control is enabled, the control signal generator 404 provides signals to the second input handle servo mechanism to orient the second input handle 624 to correspond to the orientation of the input handle 224 that is presently controlling the surgical instrument 204. This prepares the second input handle 624 to be engaged to control the surgical instrument 204 at which time the first input handle 224 may be disengaged. This may allow a smooth hand-off of the surgical instrument from one of the surgeon's hands to the other.

At other times both handles may remain engaged with one handle 224 controlling the surgical instrument 204 and the other handle 624 being controlled to maintain the corresponding orientation. The surgeon may switch between the two handles as need to perform procedures that require a greater range of motion than can be accommodated with one hand, such as moving the surgical tool 204 around an anatomical structure from back to front, across, and to the back from the other side. In one in embodiment, a manual movement of either handle 224, 624 will cause a corresponding change of orientation of the other handle so that control may be passed between handles without the need for additional action on the part of the surgeon.

Figure 7:
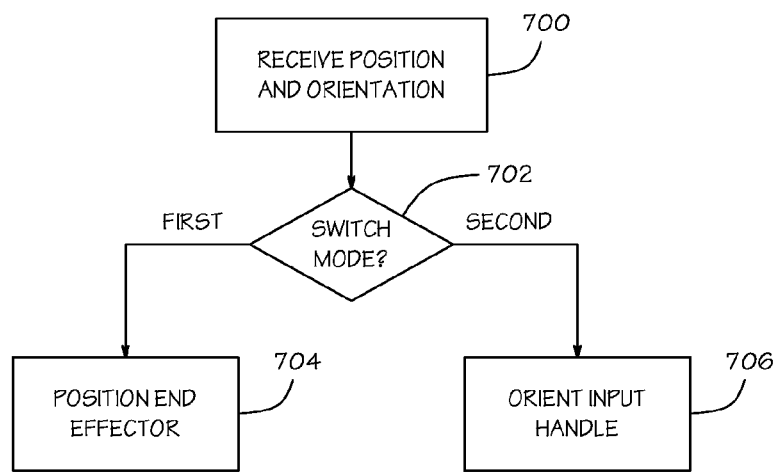
FIG. 7 is a flowchart for a method of controlling a robotic surgical system.

FIG. 7 is a flowchart for a method of controlling a robotic surgical system. An input handle position signal is received as an input handle is translated in a plurality of degrees of freedom and an input handle orientation signal is received as the input handle is rotated in a plurality of degrees of freedom 700. One of a first mode and a second mode is selected responsive to a switch 702.

If the first mode is selected, signals are provided to a first robotic manipulator to position a surgical end effector in response to the input handle position signal and the input handle orientation signal 704.

If the second mode is selected, repositioning at least one of the input handle position, the surgical end effector, or the endoscopic camera is allowed and signals are provided and to an input handle servo mechanism to continuously orient the input handle to correspond to an orientation of the surgical end effector from a viewpoint of an endoscopic camera during the repositioning 706.

In one embodiment, repositioning of the surgical end effector independently from the input handle is allowed. In another embodiment, repositioning of the endoscopic camera is allowed. In yet another embodiment, signals are provided to a second robotic manipulator to position the endoscopic camera in response to the input handle position signal. In some of these embodiments, signals may be provided to the input handle servo mechanism to prevent changes in the position of the input handle, while allowing at least one of the surgical end effector or the endoscopic camera to be repositioned. In another embodiment, translational repositioning of the input handle is allowed and movement of the end effector is inhibited.

In another embodiment, a transfer control is provided that when enabled causes signals to be provided to a second input handle servo mechanism to orient the second input handle in response to the input handle orientation signal from the first input handle.

In still another embodiment, the control system allows the repositioning of anyone of input handle, endoscopic camera, surgical instrument, PSM or PSM set up joint to happen at the same time the surgeon is controlling the motion of the surgical end effector with the master input handle. In such embodiment, in addition to the surgeon manipulating the input handle, signals are provided to the input handle servo mechanism to continuously orient the input handle to correspond to an orientation of the surgical end effector from a viewpoint of an endoscopic camera While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A robotic surgical system comprising:
a master controller with an input handle, the input handle translatable in a first plurality of degrees of freedom to provide an input handle position signal and rotatable in a second plurality of degrees of freedom to provide an input handle orientation signal, the input handle including one or more active joints that can establish the orientation of the input handle;
a first robotic manipulator including a surgical end effector movable in a third plurality of degrees of freedom;
a second robotic manipulator including an endoscopic camera movable in a fourth plurality of degrees of freedom;
a control system coupling the master controller to the first and second robotic manipulators and to the one or more active joints of the input handle, the control system providing signals to the first robotic manipulator to position the surgical end effector in response to the input handle position signal and the input handle orientation signal, and providing signals to the input handle active joints to continuously orient the input handle to correspond to an orientation of the surgical end effector from a viewpoint of the endoscopic camera during the repositioning of at least one of the input handle position, the surgical end effector, or the endoscopic camera.

2. The robotic surgical system of claim 1, wherein the control system has first and second modes, the control system providing signals to position the surgical end effector in response to the input handle position signal and the input handle orientation signal only in the first mode, and providing signals to continuously orient the input handle during the repositioning of at least one of the input handle position, the surgical end effector, or the endoscopic camera only in the second mode.

3. The robotic surgical system of claim 2, wherein the control system in the second mode is configured to allow repositioning of the surgical end effector independently from the input handle.

4. The robotic surgical system of claim 2, wherein the control system in the second mode is configured to allow repositioning of the endoscopic camera.

5. The robotic surgical system of claim 2, wherein the control system in a third mode provides signals to the second robotic manipulator to position the endoscopic camera in response to the position of the input handle position signal.

6. The robotic surgical system of claim 2, wherein the control system in the second mode is configured to allow repositioning of at least one of the surgical end effector or the endoscopic camera and prevent changes in the position of the input handle.

7. The robotic surgical system of claim 2, wherein the control system in a third mode is configured to allow translational repositioning of the input handle and inhibit movement of the surgical end effector.

8. The robotic surgical system of claim 2, wherein the master controller further includes a transfer control and a second input handle and the control system in the first mode provides signals to orient the second input handle according to the input handle position signal and the input handle orientation signal if the transfer control is enabled.

9. A controller for a robotic surgical system comprising:
a receiver coupled to an input handle, the receiver to receive an input handle position signal as the input handle is translated in a first plurality of degrees of freedom and an input handle orientation signal as the input handle is rotated in a second plurality of degrees of freedom; and
a control signal generator coupled to a first robotic manipulator that moves a surgical end effector and to an input handle servo mechanism that orients the input handle, the control signal generator to provide signals to the first robotic manipulator to position the surgical end effector in response to the input handle position signal and the input handle orientation signal, and to provide signals to the input handle servo mechanism to continuously orient the input handle to correspond to an orientation of the surgical end effector from a viewpoint of an endoscopic camera during the repositioning of at least one of the input handle position, the surgical end effector, or the endoscopic camera.

10. The controller of claim 9 further comprising a mode control coupled to a switch, the mode control to select one of a first mode and a second mode responsive to the switch, wherein the control signal generator provides signals to the first robotic manipulator to position the surgical end effector in response to the input handle position signal only in the first mode and provides signals to the input handle servo mechanism to continuously orient the input handle only in the second mode.

11. The controller of claim 10, wherein if the second mode is selected, the control signal generator is further to allow repositioning of the surgical end effector independently from the input handle.

12. The controller of claim 10, wherein if the second mode is selected, the control signal generator is further to allow repositioning of the endoscopic camera.

13. The controller of claim 10, wherein if a third mode is selected, the control signal generator is further to provide signals to a second robotic manipulator to position the endoscopic camera in response to the input handle position signal.

14. The controller of claim 10, wherein if the second mode is selected, the control signal generator is further to provide signals to the input handle servo mechanism to prevent changes in the position of the input handle and to allow repositioning of at least one of the surgical end effector or the endoscopic camera.

15. The controller of claim 10, wherein if a third mode is selected, the control signal generator is further to provide signals to the first robotic manipulator to inhibit movement of the surgical end effector and to allow translational repositioning of the input handle.

16. The controller of claim 10, further comprising a transfer control, wherein the control signal generator is further coupled to a second input handle servo mechanism that orients a second input handle, and if the first mode is selected and the transfer control is enabled, the control signal generator is further to provide signals to the second input handle servo mechanism to orient the second input handle to correspond to the orientation of the input handle.

17. A method of controlling a robotic surgical system, the method comprising:
receiving an input handle position signal as an input handle is translated in a first plurality of degrees of freedom and an input handle orientation signal as the input handle is rotated in a second plurality of degrees of freedom;
providing signals to a first robotic manipulator to position a surgical end effector in response to the input handle position signal and the input handle orientation signal; and
providing signals to an input handle servo mechanism to continuously orient the input handle to correspond to an orientation of the surgical end effector from a viewpoint of an endoscopic camera during a repositioning of at least one of the input handle position, the surgical end effector, or the endoscopic camera.

18. The method of claim 17 further comprising selecting one of a first mode and a second mode responsive to a switch, providing signals to the first robotic manipulator to position the surgical end effector in response to the input handle position signal if the first mode is selected, and providing signals to the input handle servo mechanism to continuously orient the input handle if the second mode is selected.

19. The method of claim 18 further comprising, if the second mode is selected, allowing the surgical end effector to be repositioned independently from the input handle.

20. The method of claim 18 further comprising, if the second mode is selected, allowing the endoscopic camera to be repositioned.

21. The method of claim 18 further comprising, if a third mode is selected, providing signals to a second robotic manipulator to position the endoscopic camera in response to the input handle position signal.

22. The method of claim 18 further comprising, if the second mode is selected, providing signals to the input handle servo mechanism to prevent changes in the position of the input handle, and allowing at least one of the surgical end effector or the endoscopic camera to be repositioned.

23. The method of claim 18 further comprising, if a third mode is selected, allowing translational repositioning of the input handle and inhibiting movement of the surgical end effector.

24. The method of claim 18 further comprising, if the first mode is selected and a transfer control is enabled, providing signals to a second input handle servo mechanism to orient a second input handle in response to the input handle orientation signal.

25. A control system for a robotic surgical system comprising:
means for effecting corresponding movement of a surgical end effector movable in a plurality of degrees of freedom in response to a position and an orientation of an input handle; and
means for continuously orienting the input handle to correspond to an orientation of the surgical end effector from a viewpoint of the endoscopic camera during the repositioning of at least one of the input handle position, the surgical end effector, or the endoscopic camera.

26. The control system of claim 25 further comprising means for selecting one of a first mode and a second mode, wherein the means for effecting corresponding movement of a surgical end effector in response to the position and orientation of the input handle is operative in the first mode and the means for continuously orienting the input handle during the repositioning of at least one of the input handle position, the surgical end effector, or the endoscopic camera is operative in the second mode.

27. The control system of claim 26 further comprising means, operative in the second mode, for allowing the surgical end effector to be repositioned independently from the input handle.

28. The control system of claim 26 further comprising means, operative in the second mode, for allowing the endoscopic camera to be repositioned.

29. The control system of claim 26 further comprising means, operative in a third mode, for providing signals to a second robotic manipulator to position the endoscopic camera in response to the input handle position signal.

30. The control system of claim 26 further comprising means, operative in the second mode, for providing signals to the input handle servo mechanism to prevent changes in the position of the input handle, and allowing at least one of the surgical end effector or the endoscopic camera to be repositioned.

31. The control system of claim 26 further comprising means, operative in a third mode, for allowing translational repositioning of the input handle and inhibiting movement of the surgical end effector.

32. The control system of claim 26 further comprising means, operative in the first mode, for providing signals to a second input handle servo mechanism to orient a second input handle in response to the input handle orientation signal if a transfer mode is enabled.

* * * * *